(12) United States Patent
Svirsky

(10) Patent No.: US 7,908,012 B2
(45) Date of Patent: Mar. 15, 2011

(54) COCHLEAR IMPLANT FITTING SYSTEM

(75) Inventor: Mario A. Svirsky, New York, NY (US)

(73) Assignee: New York University, New York, NY (US)

( * ) Notice: Subject to any disclaimer, the term of this patent is extended or adjusted under 35 U.S.C. 154(b) by 554 days.

(21) Appl. No.: 12/128,312

(22) Filed: May 28, 2008

(65) Prior Publication Data

US 2008/0300653 A1 Dec. 4, 2008
US 2009/0177246 A2 Jul. 9, 2009

Related U.S. Application Data

(60) Provisional application No. 60/941,053, filed on May 31, 2007.

(51) Int. Cl.
*A61N 1/00* (2006.01)
(52) U.S. Cl. ............................................ 607/57; 607/59
(58) Field of Classification Search ............... 607/55–57, 607/59
See application file for complete search history.

(56) References Cited

OTHER PUBLICATIONS

Svirsky et al., "A New Tool to Select Frequency-to-Electrode Maps for Auditory Prostheses," Aug. 2007, CIAP 2007, 43 pages.
Fitzgerald et al., "Customized Selection of Frequency Maps in an Acoustic Simulation of Bilateral Cochlear Implants," Aug. 2007, CIAP 2007, 24 pages.
Svirsky et al., "Learning to Understand Frequency-Shifted, Spectrally Degraded Speech," Jun. 2006, Rochester 2006, 40 pages.
Fitzgerald et al., "Learning to Understand Frequency-Shifted, Spectrally Degraded Speech," Apr. 2008, Milan, Italy, 48 pages.

*Primary Examiner* — Scott M Getzow
(74) *Attorney, Agent, or Firm* — Fay Kaplun & Marcin, LLP

(57) ABSTRACT

A method comprises adjusting baseline auditory stimulation parameters of a cochlear implant on a living body and providing auditory electrical stimulation to a living body via electrodes of the cochlear implant in combination with adjusting the auditory stimulation parameters of the cochlear implant to the living body in real time, retaining a database of used auditory stimulation parameters for a patient and selecting, in real time, from the database a desired one of the stimulation parameters that produces desired hearing percepts in a patient.

18 Claims, 3 Drawing Sheets

COCHLEAR IMPLANT FITTING SYSTEM

PRIORITY CLAIM

This application claims the priority to the U.S. Provisional Application Ser. No. 60/941,053, entitled "Cochlear Implant Fitting System," filed May 31, 2007. The specification of the above-identified application is incorporated herewith by reference.

FIELD OF THE INVENTION

The present invention relates to a system and method for the electrical stimulation and frequency mapping of an installed cochlear implant.

BACKGROUND INFORMATION

Cochlear implants ("CI"s) may restore the ability to hear to deaf or partially deaf individuals by providing electrical stimulation to the auditory nerve via a series of electrodes placed in the cochlea. Sound input activates the electrodes of the CI with different frequency bands being assigned to the various electrodes based on the tonotopic organization of the inner ear. The placement of each electrode within the cochlea is related to the range and value of each frequency band, with electrodes closer to the base of the cochlea generally corresponding to higher frequency bands. CIs may successfully provide the ability of almost all postlingually deaf users (i.e., those who lost their hearing after learning speech and language) to gain an auditory understanding of an environment and/or restore hearing to a level suitable for an individual to understand speech without the aid of lipreading.

After the CI is put in place, sound is picked up by a microphone and sent via a speech processor of the CI to the electrodes. After implantation, it often takes an audiologist several months of fine-tuning (and it takes the patient several months of experience with the CI) before the full efficacy of the CI is reached. Even after programming has been completed, the distortion of auditory input associated with CI's (e.g., spectral degradation and frequency shift) often requires extensive perceptual learning on the part of the patient. Spectral degradation in the CI is caused by the limited number of stimulation channels while frequency shift results from physical limitations on the electrode insertion depth which may cause a mismatch between the speech processor's analysis filters and the characteristic frequency of the neurons stimulated by the electrodes.

Stimulation parameters for the CI include a frequency map which determines the electrodes to be stimulated in response to sound of a given frequency. Most patients undergoing electrical auditory stimulation are presented with a standard frequency map.

SUMMARY OF THE INVENTION

The present invention is directed to a system and method for the real-time electrical stimulation of a cochlear implant implanted in a patient. Furthermore, the present invention is directed to the creation of a frequency map containing the stimulation parameters for the patient, wherein the frequency map may be adjusted by a user of the system of the present invention in real time while the CI is providing electrical stimulation to the patient.

The present invention is further directed to a method comprising adjusting baseline auditory stimulation parameters of a cochlear implant on a living body and providing auditory electrical stimulation to a living body via an electrode of the cochlear implant in combination with adjusting the auditory stimulation parameters of the cochlear implant to the living body in real time, retaining a database of used auditory stimulation parameters for a patient and selecting, in real time, from the database a desired one of the stimulation parameters that produces desired hearing percepts in a patient.

DETAILED DESCRIPTION

Figure 1:
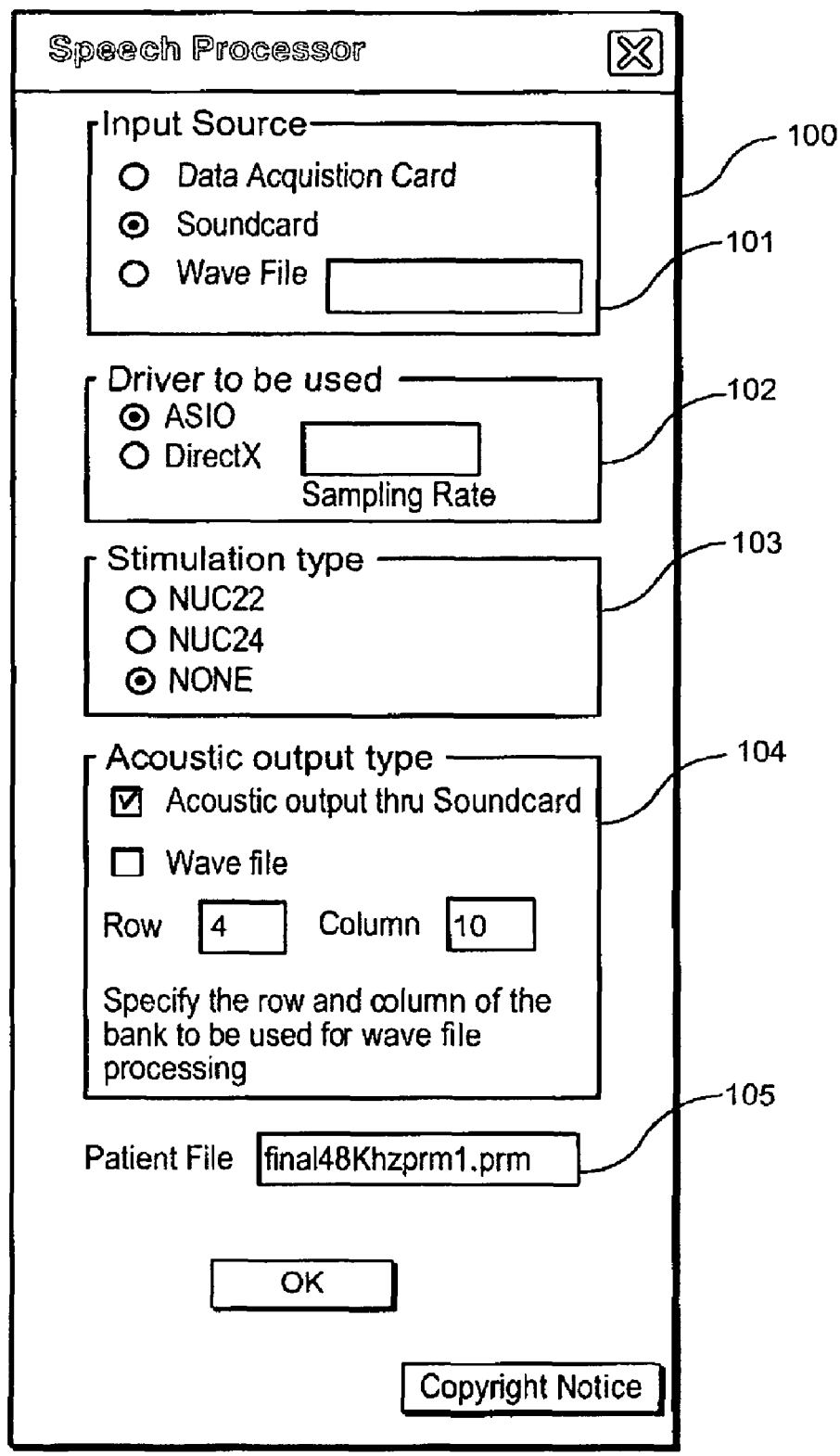
FIG. 1 shows an exemplary embodiment of an initial user interface of the present invention.

The present invention may be further understood with reference to the following description and the appended drawings. An exemplary embodiment of the present invention is directed to a system and method for providing stimulation information to a CI in real time, to facilitate the selection of a frequency-to-electrode map suited to the auditory requirements for a patient.

Under conventional CI techniques, several months are required for a patient to reach an asymptotic level of speech perception. As described above, conventional CIs distort auditory input due to frequency mismatch between the speech processor's analysis filters and the characteristic frequency of the stimulated neurons resulting from physical limitations in electrode insertion depth. In accordance with the exemplary embodiment of the present invention, a user of the CI is allowed to select a preferred frequency-to-electrode map, under the assumption that the user of the CI is best suited to select a frequency-to-electrode map minimizing frequency mismatch.

After implantation, audiologists often spend several months fine-tuning the CI before its full efficacy is reached. Each electrode in the CI may need to be fine-tuned to threshold listening levels separately. As each electrode is turned on, very small increases of electrical current are delivered to the hearing nerve until the patient hears a soft beep or tone. Once the softest hearing level is set, the patient listens for an increase in loudness until these beeps or tones become comfortable to hear. These steps are repeated in accordance with a general stimulation pattern until all electrodes have been set for soft and comfortable levels.

Since there are no general characteristic frequencies for stimulated neurons which are valid across the population, the exemplary embodiment of the present invention seeks to identify these frequencies on an individual basis by creating individualized frequency-to-electrode maps during a real time electrical stimulation for each patient. The ability to create individual frequency-to-electrode maps in real time is useful not only to reduce the time required for an audiologist to program a CI, but also to increase the efficacy of the CI by customizing its response to suit an individual's auditory incapabilities. Furthermore, the exemplary embodiment of the present invention allows a patient to adjust parameters of the frequency-to-electrode map themselves during the stimulation process by adjusting a filter bank of the CI via a user interface, as will be described in greater detail below.

By subjecting the patient to specific sound frequencies, which, in turn elicit electrical activity in the CI, a proper hearing level is determined. Furthermore, by playing a succession of different sounds to the patient, the present invention enhances the accuracy of comparisons between different stimuli by minimizing the time between the stimuli to be compared such as during a flicker or inter-stimulus interval ("ISI") of 60-70 ms. For example, it is well known in the art that, in the auditory domain, the ability to discriminate between different speech sounds is significantly better when the ISI is 250 ms as opposed to an ISI of 2 sec. Similar results have also been obtained with non-speech sounds, as both frequency and intensity-discrimination thresholds are better with ISI's of 500 ms than with ISI's of 8 sec.

The widespread decrements in discriminability that occur with increasing ISI enable patients to compare different frequency maps significantly more accurately when they are presented with a series of frequency maps in a quick sequence while listening to running speech. The frequency mapping system of the present invention allows the comparison of dozens of frequency maps within minutes—at least an order of magnitude faster than the rate possible with available clinical tools.

Furthermore, the exemplary embodiment of the present invention processes an acoustic auditory signal in real time and provides output in the form of acoustic stimulation patterns for the CI. Specifically, an input signal detected by the CI is separated into several frequency components using tools such as digital filtering, the Fast Fourier Transform or any other suitable means known to those skilled in the art. The amplitude of each of the separated frequency components is then used to determine the stimulation amplitude for waveforms sent to each electrode in the CI, and/or to determine the amplitude of noise bands that are used to acoustically simulate the auditory percepts of a CI patient.

The exemplary embodiment of the present invention allows a clinician, audiologist or CI user to change frequency maps associating acoustic frequency ranges to specific intracochlear electrodes in real time, as opposed to using a frequency mapping technique that requires programming over an extended period of time. Once a patient has recovered sufficiently after implantation of a CI, the frequency mapping method of the present invention may be employed. In accordance with the exemplary method, the initial execution may involve connecting the external portion of the CI to the appropriate stimulation hardware, as is well known to those skilled in the art. In the exemplary method described herein, the CI may be connected to a personal computer ("PC") or other suitable device whereby variables for the stimulation method may be programmed via a user-interface.

Once the CI has been connected to the PC, the audiologist selects and adjusts the parameters for the stimulation pattern. FIG. 1 shows an exemplary initial user interface 100 of a speech processor of the frequency mapping system according to the present invention. Initially, an audio input source may be selected by the audiologist from a first selection box 101. In an exemplary embodiment, the audiologist chooses between a selection of audio input sources (e.g., soundcard, data acquisition ("DAQ") card, wave file, etc.), as those skilled in the art will understand. The audio input source serves as a source of sound signals which are converted to the electrical stimulation signals sent to the electrodes of the CI. A second selection box 102 allows the audiologist to select a driver to be used where necessary for analog to digital ("A/D") and/or digital to analog ("D/A") conversion. In the exemplary embodiment shown, the audiologist may select between an Audio Stream Input Output ("ASIO") driver, and a DirectX driver. Those skilled in the art will understand that any suitable driver that provides an interface between the speech processor and the sound input source of the PC may be used. The audiologist may then select a sampling rate for the input signal as will be described in greater detail below.

The audiologist may now select the stimulation type for the procedure from a third selection box 103. The stimulation type determines whether stimulation data will be sent to the CI. In the exemplary embodiment shown, a user may select to stimulate one of two different CIs, NUC 22 and NUC 24 indicative of the type of cochlear implant the patient may have. Alternatively, the audiologist may select not to stimulate either ear, such as when testing is being performed. When this button is selected, no output is sent to the CI.

The audiologist may then select an acoustic output type from a fourth selection box 104. For example, the audiologist may send the acoustic output to disk by selecting the "Wave file" option or play the acoustic output through the sound card by selecting the "Acoustic output through Soundcard" option.

The audiologist may also select the row and column of the filter bank frequency-to-electrode map for the stimulation. The speech processor of the present invention may load a large number of frequency-to-electrode maps, with each frequency-to-electrode map organized in a matrix by row and column and with each position in the matrix being representative of a different frequency-to-electrode map. When the speech processor is used in an offline mode (i.e., where the acoustic output type is a wave or other sound file) the row and column boxes indicate which frequency-to-electrode map will be used. When the program is used in a real time mode (i.e., one of the soundcard, DAQ card, etc. is selected as the input source), the row and column boxes indicate the initial frequency-to-electrode map to be used when the stimulation commences. Accordingly, in the exemplary method of the present invention, the audiologist or the patient or any other operator of the system may move around the matrix of frequency-to-electrode maps and change frequency-to-electrode map selections in real time.

Lastly, the audiologist may select a patient file to load from a fifth selection box 105. The patient file contains parameters specific to a patient including, but not limited to, a stimulation strategy, frequency-to-electrode map, a stimulation rate, channels to be stimulated, input dynamic range as well as threshold and comfortable electrical stimulation levels for each channel. The patient file may store the aforementioned files by date and instance of stimulation. For example, a user may save parameters to the patient file each time a stimulation is performed. The audiologist may also reference the file to determine how many stimulations have been performed on a patient as well the specific parameters used in each stimulation.

Figure 2:
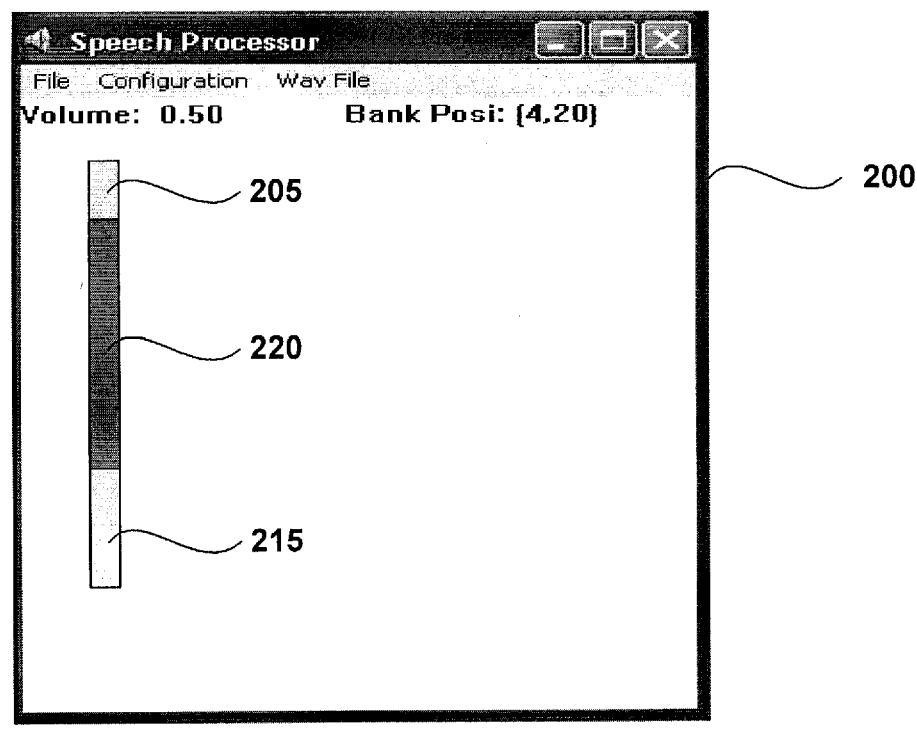
FIG. 2 shows an exemplary embodiment of the user interface for filter bank adjustment of the present invention.

FIG. 2 shows an exemplary embodiment of an initial screen an audiologist or patient may see at the beginning of a frequency-to-electrode map adjustment task. A dark rectangle 220 represents the frequency range covered by the active frequency-to-electrode map, whose output is heard by the patient in real time. In an exemplary embodiment, the frequency-to-electrode map bank covers frequencies ranging from 850 Hz to 17,000 Hz. Employment of a large number of frequency-to-electrode maps allows the audiologist to select ranges best suited for the patient's auditory incapabilities. The dark rectangle 220 plus the two additional rectangles 205 and 215 in a lighter color, placed above and below the dark rectangle 220 respectively, represent the total frequency range audible to humans. One possible frequency scale that may be used for this graphical representation is determined by Greenwood's Function, which states that frequency is a function of the specific location within the cochlea. In other words, the length of each of the rectangles represents a distance along the cochlea.

During the stimulation, the patient or audiologist uses a keyboard or other suitable interface of the PC to change the active frequency-to-electrode map indicated by the dark rectangle 220. Appropriate controls such as, for example, the arrow keys on a computer keyboard, may be used to increase or decrease the frequency range of the frequency-to-electrode map (i.e., the length of the dark rectangle 220), while leaving the midpoint constant. Such a change may show up in the display as either an expansion or a contraction of the dark rectangle 220. Alternate controls may be used to move the entire active frequency-to-electrode map up or down in frequency while leaving the extent of the frequency range constant. In this case, the dark rectangle 220 may be moved up or down in the display while its length remains constant. The capability to change the extent and/or the mid-point of the frequency range during stimulation provides a greater degree of accuracy and efficiency than afforded by currently available systems. It is also possible to use other controls to change other characteristics of the frequency-to-electrode map, not just the extent and mid-point of the frequency range.

The dark rectangle 220 which is representative of the entire frequency-to-electrode map relative to the chosen stimulation parameters may be subdivided into a number of frequency subranges, with each subrange being indicative of a filter in the frequency-to-electrode map. In an exemplary embodiment, a range of 8 to 22 filters may be used in the frequency-to-electrode map. However, it is noted that this is only an exemplary embodiment and, in function, any number of plurality of filters may be used.

It is noted that, while an operator of the system changes the frequency-to-electrode map, speech processing continues without perceptible interruption. Therefore, the patient may make immediate and precise assessments concerning the relative intelligibility and sound quality of the various frequency-to-electrode maps tested. Using such a system increases accuracy and reduces perceptual problems that may be caused by using larger ISIs in the stimulation, as discussed earlier. As those skilled in the art will understand, employment of a system wherein a continuous acoustic or electrical stimulation is used, the ISI is substantially reduced to zero.

Figure 3:
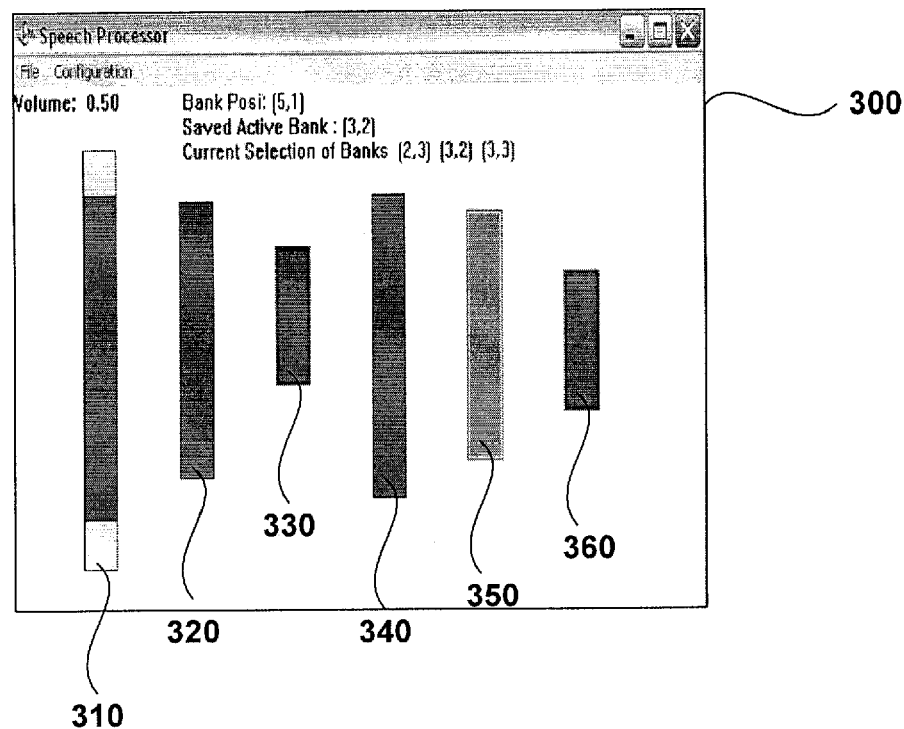
FIG. 3 shows an exemplary embodiment of the user interface for filter bank adjustment of the present invention after several filter banks have been selected and one of them is active.

In addition to the continuous adjustment described above, the patient or audiologist may also select a number of frequency-to-electrode maps for further comparison. For example, as shown in FIG. 3, after a user of the speech processor has selected a frequency-to-electrode map 320 in accordance with the procedure noted above, the frequency-to-electrode map 320 may be placed on a screen alongside a real-time frequency-to-electrode map adjuster 310, as shown in FIG. 3. This procedure may be repeated with any plurality of frequency-to-electrode maps, such as frequency-to-electrode maps 330-360. A user of the speech processor of the present invention may align the plurality of frequency-to-electrode maps 320-360 on one window using a simple copying technique (e.g., by making a selection from a drop-down menu or other means known in the art). Alternatively, the plurality of frequency-to-electrode maps 320-360 may be added automatically on an individual basis once a frequency-to-electrode map has been chosen. This may allow a user of the speech processor to quickly and accurately compare the plurality of frequency-to-electrode maps to discover what changes may enhance the performance of the CI.

The availability of the real-time frequency-to-electrode map adjuster allows an operator of the system to customize a frequency-to-electrode map incorporating any desired changes identified during the testing procedure. The operator may scroll through the plurality of frequency-to-electrode maps 310-360 via the user interface of the PC such as, for example, by pressing the space bar. The active frequency-to-electrode map may be highlighted by any of a number of means such as with a border or color change of the frequency-to-electrode map, as is shown with respect to the active frequency-to-electrode map 350 in FIG. 3.

Figure 4:
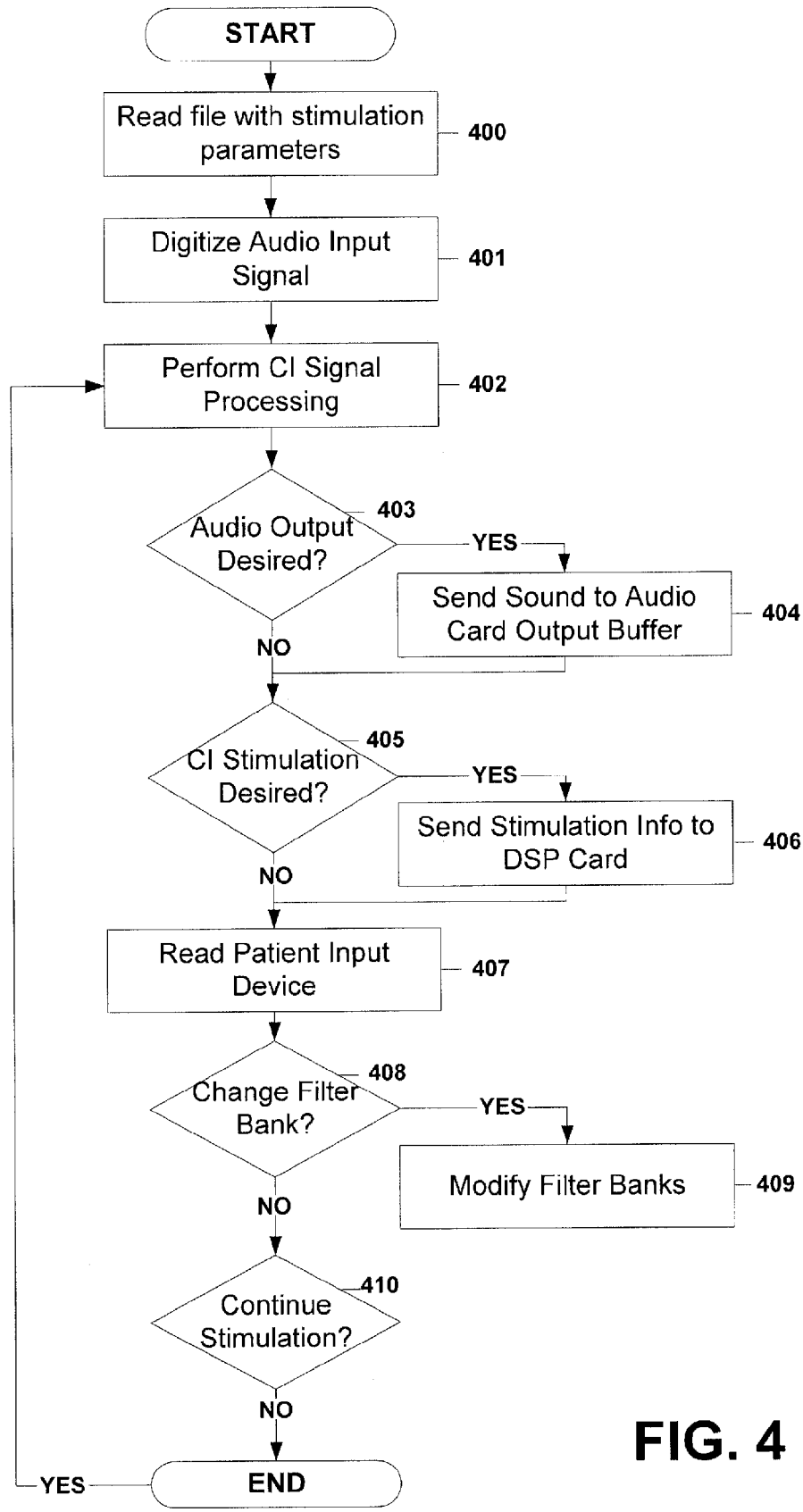
FIG. 4 shows an exemplary embodiment of a method according to the present invention.

An exemplary method of the present invention as described with respect to FIG. 4 begins by allowing an operator of the system to select a patient file to begin stimulation. In step 400, a user interface based on a PC or other data processing apparatus may be used to read the patient file which stores parameters for the stimulation. These parameters may include, but are not limited to, stimulation strategy, frequency-to-electrode map, minimum and maximum stimulation levels for each channel, stimulation rate, input dynamic range, filters for filter banks, etc. In step 401, the system begins digitizing the audio input signal produced based on the stimulation parameters provided by an operator.

In step 402, the system of the present invention begins CI signal processing including, for example, making determinations of stimulus pulse amplitudes, filtering or frequency transform calculations, automatic gain control, pre-emphasis, etc., as those skilled in the art will understand. A parameter read during step 400 determines if audio output is desired in step 403. As described above, the operator may not desire audio output and in this case the method proceeds to step 405. However, if the operator elects to have audio output, the method continues to step 404, where the sound signal is sent to the audio card output buffer of the system, as those skilled in the art will understand.

The method then proceeds to step 405, in which the operator decides whether CI stimulation is desired, as also described earlier. If the operator elects to use CI stimulation, such as when a real-time stimulation is being performed, the method proceeds to step 406, wherein the stimulation is sent to an appropriate interface which may be based on a Digital Signal Processor ("DSP") card and may include additional hardware depending on the specific cochlear implant used by the patient. The DSP card provides real-time digital signal processing of the audio signal, as those skilled in the art will understand. The output of the interface including the DSP Card is connected to a transmitter coil placed on the patient's head. This coil transmits stimulation information to the implanted device. If no CI stimulation is desired, the method may proceed to step 407, wherein the system reads the user interface device such as the PC to determine whether changes have been made to the stimulation parameters during the real-time stimulation. Because the present invention operates in real-time, any changes made to the parameters are immediately reflected in the stimulation.

Step 408 determines if any changes have been made to the filter bank, as shown with respect to FIGS. 2 and 3. If no changes have been made, the method may continue. If changes have been made, the filter banks in the system are updated to reflect the change in step 409. The operator decides whether to stop stimulation by providing an appropriate instruction to the program. Unless the operator decides to stop, the method returns to step 402 wherein CI signal processing continues. Otherwise, if the operator elects not to continue processing, the method ends.

The exemplary embodiment of the present invention may be used by patients who have one cochlear implant, with or without residual hearing, and patients who use bilateral cochlear implants. Other embodiments of the invention will be apparent to those skilled in the art from consideration of the specification and practice of the invention disclosed herein. Thus, it is intended that the present invention cover the modifications and variations of this invention provided they come within the scope of the appended claims and their equivalents.

What is claimed is:

1. A method, comprising:
    adjusting baseline auditory stimulation parameters of a cochlear implant on a living body,
    providing auditory electrical stimulation to a living body via a plurality of electrodes of the cochlear implant;
    adjusting the auditory stimulation parameters of the cochlear implant to the living body in real time;
    retaining a database of used auditory stimulation parameters for a patient; and
    selecting, in real time, from the database a desired one of the stimulation parameters that produces desired hearing percepts in a patient.

2. The method of claim 1, wherein the auditory stimulation parameters include at least one of stimulation strategy, frequency-to-electrode map range, stimulation sampling rate, channels to be stimulated, input dynamic range, threshold and comfortable electrical stimulation levels for each channel.

3. The method according to claim 1, further comprising:
    providing a patient with a real time adjustable frequency-to-electrode map to adjust the active frequency range for the cochlear implant.

4. The method according to claim 3, further comprising:
    retaining used frequency-to-electrode maps for a patient; and
    selecting from the list of frequency-to-electrode maps a frequency-to-electrode map that produces the desired hearing percepts in a patient.

5. The method of claim 1, further comprising:
    using one of digital filtering and Fast Fourier Transform Analysis to separate the input sound signal into several frequencies.

6. The method of claim 1, wherein the electrodes stimulate auditory neurons of the cochlea.

7. The method of claim 1, further comprising:
    sequentially providing electrical stimulation to at least one of the electrodes with an interstimulus interval of less than 100 ms.

8. The method of claim 1, further comprising:
    adjusting the stimulation parameters to a level where a threshold hearing level is defined.

9. The method of claim 1, further comprising:
    performing multiple electrical stimulations referencing a database for a patient.

10. The method of claim 1, wherein the auditory electrical stimulation is provided continuously via the electrodes.

11. The method of claim 1, wherein the desired hearing percepts are most intelligible hearing percepts.

12. A system for electrically stimulating a cochlear implant, comprising:
    an electrode contact transmitting electrical stimuli from stimulation hardware to the cochlear implant;
    a component establishing frequency-to-electrode maps for each of a plurality of stimulation parameters of the electrical stimuli provided by the stimulation hardware;
    a user-interface component permitting a user to adjust the stimulation parameters in real time;
    a component storing the frequency-to-electrode maps; and
    a component comparing multiple frequency-to-electrode maps to determine a most desired frequency-to-electrode map.

13. The system according to claim 12, wherein the auditory stimulation parameters include at least one of stimulation strategy, frequency-to-electrode map range, stimulation sampling rate, channels to be stimulated, input dynamic range, threshold and comfortable electrical stimulation levels for each channel.

14. The system according to claim 12, further comprising:
    a component providing real-time adjustable frequency-to-electrode maps facilitating adjustment of an active frequency range of the cochlear implant.

15. The system according to claim 12, further comprising:
    a component selectively selecting the most desired frequency-to-electrode map.

16. The system according to claim 12, further comprising:
    a component separating input sound signals into several frequencies by one of digital filtering and Fast Fourier Transform Analysis.

17. The system according to claim 12, wherein the electrical stimulation is provided from the electrode contact to an electrode of the cochlear implant with an interstimulus interval of no more than 100 ms.

18. A computer readable storage medium including instructions which, when executed by a processor, directs the processor to perform the following steps:
    adjusting baseline auditory stimulation parameters of a cochlear implant on a living body;
    providing auditory electrical stimulation to a living body via a plurality of electrodes of the cochlear implant;
    adjusting the stimulation parameters of the cochlear implant to the living body in real time;
    retaining a database of used auditory stimulation parameters for a patient; and
    selecting, in real time, from the database a desired one of the stimulation parameters that produces desired hearing percepts in a patient.

* * * * *